US012629220B2

(12) United States Patent
Abbott

(10) Patent No.: US 12,629,220 B2
(45) Date of Patent: *May 19, 2026

(54) JOINTED CONTROL PLATFORM

(71) Applicant: Intuitive Surgical Operations, Inc., Sunnyvale, CA (US)

(72) Inventor: Ryan C. Abbott, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 635 days.

This patent is subject to a terminal disclaimer.

(21) Appl. No.: 17/953,898

(22) Filed: Sep. 27, 2022

(65) Prior Publication Data

US 2023/0119001 A1 Apr. 20, 2023

Related U.S. Application Data

(63) Continuation of application No. 16/269,159, filed on Feb. 6, 2019, now Pat. No. 11,497,567.

(Continued)

(51) Int. Cl.
A61B 34/30 (2016.01)
A61B 34/00 (2016.01)
(Continued)

(52) U.S. Cl.
CPC .............. A61B 34/30 (2016.02); A61B 34/20 (2016.02); A61B 34/70 (2016.02); A61B 34/71 (2016.02);
(Continued)

(58) Field of Classification Search
CPC ......... A61B 34/30; A61B 34/70; A61B 34/71; A61B 2017/00477; A61B 2034/302;
(Continued)

(56) References Cited

U.S. PATENT DOCUMENTS 793,510 A 6/1905 Cramer et al.
2,091,317 A 8/1937 Hill
(Continued)

FOREIGN PATENT DOCUMENTS

AU 2014208189 A1 4/2015
CN 2573759 Y 9/2003
(Continued)

OTHER PUBLICATIONS

Litvin F.L., et al., "Face Gear Drive with Helical Involute Pinion: Geometry, Generation by a Shaper and a Worm, Avoidance of Singularities and Stress Analysis," NASA/CR—2005-213443, ARL-CR-557, Feb. 2005, 62 pages.
(Continued)

*Primary Examiner* — Michael W Kahelin
*Assistant Examiner* — Karmel J Webster

(57) ABSTRACT

A medical device having a force transmission mechanism that includes a chassis having a pivotal support that defines a first axis. An axle is supported by the pivotal support and is free to rotate around the first axis of rotation. The axle defines a second axis of rotation perpendicular to the first axis of rotation. A first control arm is coupled to a first end of the axle and is free to rotate around the second axis of rotation. A second control arm is coupled to an opposite second end of the axle and is free to rotate around the second axis of rotation independently of the first control arm. A distal component is coupled to an elongate tube that is coupled to the chassis. Four drive elements coupled to the control arms control motion of the distal component. In one implementation, the medical device is a teleoperated surgical instrument.

21 Claims, 6 Drawing Sheets

Related U.S. Application Data

(60) Provisional application No. 62/628,133, filed on Feb. 8, 2018.

(51) Int. Cl.

| | |
|---|---|
| *A61B 34/20* | (2016.01) |
| *B25J 9/00* | (2006.01) |
| *B25J 9/04* | (2006.01) |
| *A61B 17/00* | (2006.01) |

(52) U.S. Cl.
CPC .............. *B25J 9/0084* (2013.01); *B25J 9/04* (2013.01); *A61B 2017/00477* (2013.01); *A61B 2034/302* (2016.02); *A61B 2034/305* (2016.02)

(58) Field of Classification Search
CPC .. A61B 2034/305; A61B 34/35; B25J 9/0084; B25J 9/04
USPC .......................................................... 606/1
See application file for complete search history.

(56) References Cited

U.S. PATENT DOCUMENTS

| | | | |
|---|---|---|---|
| 2,906,143 A | | 9/1959 | Musser |
| 4,899,608 A | | 2/1990 | Knappe et al. |
| 5,099,705 A | | 3/1992 | Dravnieks |
| 5,207,691 A | | 5/1993 | Nardella |
| 5,667,354 A | * | 9/1997 | Nakazawa ............... B25J 9/042 |
| | | | 414/744.5 |
| 5,674,024 A | | 10/1997 | Daumal et al. |
| 5,792,135 A | | 8/1998 | Madhani et al. |
| 5,807,377 A | | 9/1998 | Madhani et al. |
| 5,876,325 A | | 3/1999 | Mizuno et al. |
| 6,007,550 A | | 12/1999 | Wang et al. |
| 6,331,181 B1 | | 12/2001 | Tierney et al. |
| 6,371,952 B1 | | 4/2002 | Madhani et al. |
| 6,394,998 B1 | | 5/2002 | Wallace et al. |
| 6,817,974 B2 | | 11/2004 | Cooper et al. |
| 6,994,708 B2 | | 2/2006 | Manzo |
| 6,997,079 B2 | | 2/2006 | Nomura et al. |
| 7,090,683 B2 | | 8/2006 | Brock et al. |
| 7,169,141 B2 | | 1/2007 | Brock et al. |
| 7,214,230 B2 | | 5/2007 | Brock et al. |
| 7,331,967 B2 | | 2/2008 | Lee et al. |
| 7,371,210 B2 | | 5/2008 | Brock et al. |
| 7,524,320 B2 | | 4/2009 | Tierney et al. |
| 7,666,191 B2 | | 2/2010 | Orban, III et al. |
| 7,935,130 B2 | | 5/2011 | Williams |
| 8,142,421 B2 | | 3/2012 | Cooper et al. |
| 8,444,631 B2 | | 5/2013 | Yeung et al. |
| 8,479,969 B2 | | 7/2013 | Shelton, IV |
| 8,506,555 B2 | | 8/2013 | Ruiz Morales |
| 8,551,115 B2 | | 10/2013 | Steger et al. |
| 8,597,280 B2 | | 12/2013 | Cooper et al. |
| 8,602,288 B2 | | 12/2013 | Shelton, IV et al. |
| 8,771,270 B2 | | 7/2014 | Burbank |
| 8,800,838 B2 | | 8/2014 | Shelton, IV |
| 8,992,565 B2 | | 3/2015 | Brisson et al. |
| 9,028,494 B2 | | 5/2015 | Shelton, IV et al. |
| 9,078,684 B2 | | 7/2015 | Williams |
| 9,121,494 B2 | | 9/2015 | Buchleitner et al. |
| 9,198,714 B2 | | 12/2015 | Worrell et al. |
| 9,204,923 B2 | | 12/2015 | Manzo et al. |
| 9,232,979 B2 | | 1/2016 | Parihar et al. |
| 9,259,274 B2 | | 2/2016 | Prisco |
| 9,259,275 B2 | | 2/2016 | Burbank |
| 9,289,112 B2 | | 3/2016 | Takemoto et al. |
| 9,572,616 B2 | | 2/2017 | Vaughn |
| 9,664,262 B2 | | 5/2017 | Donlon et al. |
| 9,737,373 B2 | | 8/2017 | Schuh |
| 9,839,439 B2 | | 12/2017 | Cooper et al. |
| 9,869,339 B2 | | 1/2018 | Zimmerman et al. |
| 9,913,694 B2 | | 3/2018 | Brisson |
| 9,931,106 B2 | | 4/2018 | Au et al. |
| 9,993,313 B2 | | 6/2018 | Schuh et al. |
| 10,016,244 B2 | | 7/2018 | Cooper et al. |
| 10,022,193 B2 | | 7/2018 | Cooper et al. |
| 10,076,348 B2 | | 9/2018 | Anderson et al. |
| 10,130,366 B2 | | 11/2018 | Shelton, IV et al. |
| 10,201,365 B2 | | 2/2019 | Boudreaux et al. |
| 10,219,874 B2 | | 3/2019 | Yu et al. |
| 10,288,837 B2 | | 5/2019 | Miyatani et al. |
| 10,314,583 B2 | | 6/2019 | Smith et al. |
| 10,470,830 B2 | | 11/2019 | Hill et al. |
| 10,478,256 B2 | | 11/2019 | Shelton, IV et al. |
| 10,543,051 B2 | | 1/2020 | Schena et al. |
| 10,595,949 B2 | | 3/2020 | Donlon et al. |
| 10,624,709 B2 | | 4/2020 | Remm |
| 10,653,489 B2 | | 5/2020 | Kopp |
| 10,667,877 B2 | | 6/2020 | Kapadia |
| 10,682,141 B2 | | 6/2020 | Moore et al. |
| 10,779,898 B2 | | 9/2020 | Hill et al. |
| 10,792,112 B2 | | 10/2020 | Kokish et al. |
| 10,806,530 B2 | | 10/2020 | Liao et al. |
| 10,881,280 B2 | | 1/2021 | Baez, Jr. |
| 10,932,868 B2 | | 3/2021 | Solomon et al. |
| 11,013,566 B2 | | 5/2021 | Diel et al. |
| 11,020,112 B2 | | 6/2021 | Shelton, IV et al. |
| 11,045,270 B2 | | 6/2021 | Shelton, IV et al. |
| 11,076,926 B2 | | 8/2021 | Ragosta et al. |
| 11,118,661 B2 | | 9/2021 | Abbott |
| 11,248,686 B2 | | 2/2022 | Cooper et al. |
| 11,304,770 B2 | | 4/2022 | Crews et al. |
| 11,497,567 B2 | * | 11/2022 | Abbott ................... B25J 9/0084 |
| 11,517,397 B2 | | 12/2022 | Lambrecht et al. |
| 2002/0111635 A1 | | 8/2002 | Jensen et al. |
| 2003/0135203 A1 | | 7/2003 | Wang et al. |
| 2005/0042943 A1 | | 2/2005 | Mocivnik et al. |
| 2005/0089345 A1 | | 4/2005 | Yasumoto et al. |
| 2005/0119527 A1 | | 6/2005 | Banik et al. |
| 2007/0043338 A1 | | 2/2007 | Moll et al. |
| 2007/0232858 A1 | | 10/2007 | Macnamara et al. |
| 2008/0046122 A1 | | 2/2008 | Manzo et al. |
| 2008/0065102 A1 | | 3/2008 | Cooper |
| 2008/0065105 A1 | | 3/2008 | Larkin et al. |
| 2008/0087871 A1 | | 4/2008 | Schena et al. |
| 2008/0103491 A1 | | 5/2008 | Omori et al. |
| 2008/0196533 A1 | | 8/2008 | Bergamasco et al. |
| 2009/0088774 A1 | | 4/2009 | Swarup et al. |
| 2009/0112230 A1 | | 4/2009 | Jinno |
| 2009/0148263 A1 | | 6/2009 | Lee et al. |
| 2009/0198272 A1 | * | 8/2009 | Kerver ................... A61B 17/29 |
| | | | 606/205 |
| 2010/0011900 A1 | | 1/2010 | Burbank et al. |
| 2010/0170519 A1 | | 7/2010 | Romo et al. |
| 2010/0175701 A1 | | 7/2010 | Reis et al. |
| 2010/0318101 A1 | | 12/2010 | Choi et al. |
| 2011/0015650 A1 | | 1/2011 | Choi et al. |
| 2011/0071543 A1 | | 3/2011 | Prisco et al. |
| 2011/0118754 A1 | | 5/2011 | Dachs, II et al. |
| 2011/0184241 A1 | | 7/2011 | Zubiate et al. |
| 2011/0277580 A1 | * | 11/2011 | Cooper ................... B25J 13/00 |
| | | | 74/473.1 |
| 2011/0277775 A1 | | 11/2011 | Holop et al. |
| 2011/0295269 A1 | | 12/2011 | Swensgard et al. |
| 2011/0295270 A1 | | 12/2011 | Giordano et al. |
| 2011/0313405 A1 | | 12/2011 | Anderson et al. |
| 2012/0046522 A1 | | 2/2012 | Naito |
| 2012/0109186 A1 | | 5/2012 | Parrott et al. |
| 2012/0123441 A1 | | 5/2012 | Au et al. |
| 2012/0150144 A1 | * | 6/2012 | Campbell ......... A61M 5/14244 |
| | | | 604/500 |
| 2012/0215220 A1 | * | 8/2012 | Manzo ................... A61B 34/30 |
| | | | 606/46 |
| 2012/0239060 A1 | | 9/2012 | Orban, III et al. |
| 2012/0289974 A1 | | 11/2012 | Rogers et al. |
| 2012/0298719 A1 | | 11/2012 | Shelton, IV et al. |
| 2013/0046318 A1 | | 2/2013 | Radgowski et al. |
| 2013/0123783 A1 | | 5/2013 | Marczyk et al. |
| 2013/0144395 A1 | | 6/2013 | Stefanchik et al. |
| 2013/0267950 A1 | * | 10/2013 | Rosa ............. A61B 17/320016 |
| | | | 606/45 |
| 2014/0005662 A1 | | 1/2014 | Shelton, IV |

(56) References Cited

U.S. PATENT DOCUMENTS

| | | |
|---|---|---|
| 2014/0005678 A1 | 1/2014 | Shelton, IV et al. |
| 2014/0005708 A1 | 1/2014 | Shelton, IV |
| 2014/0100558 A1 | 4/2014 | Schmitz et al. |
| 2014/0257333 A1 | 9/2014 | Blumenkranz |
| 2014/0276723 A1 | 9/2014 | Parihar et al. |
| 2014/0309625 A1 | 10/2014 | Okamoto et al. |
| 2014/0378994 A1* | 12/2014 | Wang ...................... F16H 21/54 |
| | | 606/130 |
| 2015/0005786 A1 | 1/2015 | Burbank |
| 2015/0047454 A1* | 2/2015 | Cooper ............... A61B 1/0057 |
| | | 74/490.06 |
| 2015/0051034 A1 | 2/2015 | Cooper et al. |
| 2015/0051618 A1* | 2/2015 | Anderson ............. A61B 17/28 |
| | | 606/130 |
| 2015/0150635 A1 | 6/2015 | Kilroy et al. |
| 2015/0150636 A1 | 6/2015 | Hagn et al. |
| 2015/0157355 A1 | 6/2015 | Price et al. |
| 2015/0209965 A1 | 7/2015 | Low et al. |
| 2016/0058443 A1 | 3/2016 | Yates et al. |
| 2016/0151115 A1 | 6/2016 | Karguth et al. |
| 2016/0157926 A1 | 6/2016 | Boudreaux |
| 2016/0184034 A1 | 6/2016 | Holop et al. |
| 2016/0184037 A1 | 6/2016 | Cooper et al. |
| 2016/0199138 A1 | 7/2016 | Cooper et al. |
| 2016/0296219 A1 | 10/2016 | Srivastava et al. |
| 2016/0338762 A1 | 11/2016 | Krastins et al. |
| 2016/0361049 A1 | 12/2016 | Dachs, II et al. |
| 2017/0007345 A1 | 1/2017 | Smith et al. |
| 2017/0014998 A1 | 1/2017 | Langenfeld et al. |
| 2017/0022754 A1 | 1/2017 | Nien et al. |
| 2017/0027656 A1 | 2/2017 | Robert et al. |
| 2017/0165017 A1 | 6/2017 | Chaplin et al. |
| 2017/0172672 A1 | 6/2017 | Bailey et al. |
| 2017/0207467 A1 | 7/2017 | Shelton, IV et al. |
| 2017/0248194 A1 | 8/2017 | Bae et al. |
| 2017/0265865 A1 | 9/2017 | Burbank |
| 2018/0055583 A1 | 3/2018 | Schuh et al. |
| 2018/0214223 A1 | 8/2018 | Turner |
| 2018/0229021 A1 | 8/2018 | Donlon et al. |
| 2018/0243036 A1 | 8/2018 | Donlon et al. |
| 2019/0038282 A1 | 2/2019 | Shelton, IV et al. |
| 2019/0099227 A1 | 4/2019 | Rockrohr |
| 2019/0117325 A1 | 4/2019 | Kishi |
| 2019/0125468 A1 | 5/2019 | Adams |
| 2019/0159846 A1* | 5/2019 | Yates ...................... A61B 34/30 |
| 2019/0175887 A1 | 6/2019 | Shameli |
| 2019/0192137 A1 | 6/2019 | Shelton, IV et al. |
| 2019/0201022 A1 | 7/2019 | Schoettgen et al. |
| 2019/0223960 A1 | 7/2019 | Chaplin et al. |
| 2019/0231451 A1 | 8/2019 | Lambrecht et al. |
| 2019/0231464 A1 | 8/2019 | Wixey et al. |
| 2019/0239965 A1 | 8/2019 | Abbott |
| 2019/0298323 A1 | 10/2019 | Lambrecht et al. |
| 2019/0307522 A1* | 10/2019 | Lambrecht ............. A61B 34/30 |
| 2019/0328467 A1 | 10/2019 | Waterbury et al. |
| 2019/0374240 A1 | 12/2019 | Brodbeck et al. |
| 2020/0008828 A1 | 1/2020 | Overmyer |
| 2020/0093554 A1 | 3/2020 | Schuh et al. |
| 2020/0138473 A1 | 5/2020 | Shelton, IV et al. |
| 2020/0197117 A1 | 6/2020 | Donlon et al. |
| 2020/0261168 A1 | 8/2020 | Anglese |
| 2021/0169591 A1 | 6/2021 | Kapadia |
| 2021/0196413 A1 | 7/2021 | Inoue |
| 2021/0220001 A1 | 7/2021 | Heiliger |
| 2021/0322118 A1 | 10/2021 | Donlon et al. |
| 2021/0372508 A1 | 12/2021 | Abbott |
| 2022/0015847 A1 | 1/2022 | Kadokura |
| 2022/0039895 A1 | 2/2022 | Adams et al. |
| 2022/0096067 A1 | 3/2022 | Beckman et al. |
| 2022/0096082 A1 | 3/2022 | Beckman et al. |
| 2022/0128133 A1 | 4/2022 | Cooper et al. |
| 2023/0045998 A1 | 2/2023 | Shelton, IV et al. |
| 2024/0100942 A1 | 3/2024 | Mattsson et al. |
| 2024/0197423 A1 | 6/2024 | Ragosta et al. |
| 2025/0169899 A1 | 5/2025 | Heye |
| 2025/0186147 A1 | 6/2025 | Times et al. |

FOREIGN PATENT DOCUMENTS

| | | | | |
|---|---|---|---|---|
| CN | 109069138 A | 12/2018 | | |
| CN | 110584787 A | 12/2019 | | |
| EP | 2548529 A1 | 1/2013 | | |
| EP | 2783643 A1 | 10/2014 | | |
| EP | 3103374 A1 | 12/2016 | | |
| EP | 3195993 A1 | 7/2017 | | |
| EP | 3476321 A1 | 5/2019 | | |
| FR | 3014678 A1 | 6/2015 | | |
| JP | H06114000 A | 4/1994 | | |
| JP | H10249777 A | 9/1998 | | |
| JP | 2003024336 A | 1/2003 | | |
| JP | 2005288590 A | 10/2005 | | |
| WO | WO-9729690 A1 | 8/1997 | | |
| WO | WO-0030557 A1 | 6/2000 | | |
| WO | WO-2009039506 A1 | 3/2009 | | |
| WO | WO-2012064528 A1 | 5/2012 | | |
| WO | WO-2012068156 A2 | 5/2012 | | |
| WO | WO-2012166806 A1 | 12/2012 | | |
| WO | WO-2015142290 A1 | 9/2015 | | |
| WO | WO-2016073637 A1 | 5/2016 | | |
| WO | WO-2016161449 A1 | 10/2016 | | |
| WO | WO-2016172299 A1 | 10/2016 | | |
| WO | WO-2016189284 A1 | 12/2016 | | |
| WO | WO-2017188851 A1 | 11/2017 | | |
| WO | WO-2018013313 A1 | 1/2018 | | |
| WO | WO-2018049217 A1 | 3/2018 | | |
| WO | WO-2018094191 A1 * | 5/2018 | ............. | A61B 34/30 |
| WO | WO-2019222058 A1 | 11/2019 | | |
| WO | WO-2020102776 A1 | 5/2020 | | |
| WO | WO-2020184588 A1 | 9/2020 | | |
| WO | WO-2020252184 A1 | 12/2020 | | |
| WO | WO-2021041395 A1 | 3/2021 | | |
| WO | WO-2021155707 A1 | 8/2021 | | |
| WO | WO-2021192255 A1 | 9/2021 | | |
| WO | WO-2023177554 A1 | 9/2023 | | |

OTHER PUBLICATIONS

Litvin F.L., et al., "Handbook on Face Gear Drives with a Spur Involute Pinion," NASA/CR-2000-209909, ARL-CR-447, Mar. 2000, 106 pages.

Office Action for U.S. Appl. No. 16/269,159, mailed Feb. 25, 2022, 14 pages.

Smith L.J., "The Involute Helicoid and the Universal Gear," Gear Technology, Nov./Dec. 1990, pp. 18-27.

Stadtfeld H, Dr., "Tribology Aspects in Angular Transmission Systems: Part I—General Explanations on Theoretical Bevel Gear Analysis," Gear Technology, Aug. 2010, URL: https://www.geartechnology.com/issues/0810x/stadtfeld1.pdf , pp. 46-52.

Stadtfeld H, Dr., "Tribology Aspects in Angular Transmission Systems: Part II—Straight Bevel Gears," Gear Technology, Sep.-Oct. 2010, URL: http://www.geartechnology.com/issues/0910x/stadtfeld.pdf , pp. 47-52.

Stadtfeld H, Dr., "Tribology Aspects in Angular Transmission Systems: Part III—Zerol Bevel Gears," Gear Technology, Nov.-Dec. 2010, URL: http://www.geartechnology.com/issues/1110x/zerol.pdf , pp. 42-47.

Stadtfeld H, Dr., "Tribology Aspects in Angular Transmission Systems: Part IV—Spiral Bevel Gears," Gear Technology, Jan.-Feb. 2011, URL: https://www.geartechnology.com/issues/0111x/stadtfeld.pdf , pp. 66-72.

Stadtfeld H, Dr., "Tribology Aspects in Angular Transmission Systems: Part V—Face Gears," Gear Technology, Mar.-Apr. 2011, URL: http://www.geartechnology.com/issues/0311x/stadtfeld.pdf , pp. 47-52.

Stadtfeld H, Dr., "Tribology Aspects in Angular Transmission Systems: Part VI—Beveloid & Hypoloid Gears," Gear Technology, May 2011, URL: https://www.geartechnology.com/issues/0511x/beveloid.pdf , pp. 48-52.

(56)            References Cited

OTHER PUBLICATIONS

Stadtfeld H, Dr., "Tribology Aspects in Angular Transmission Systems: Part VII—Hypoid Gears," Gear Technology, Jun.-Jul. 2011, URL: https://www.geartechnology.com/issues/0611x/hypoid. pdf , pp. 66-72.
Stadtfeld H, Dr., "Tribology Aspects in Angular Transmission Systems: Part VIII—Super-Reduction Hypoid Gears," Gear Technology, Aug. 2011, URL: http://www.geartechnology.com/issues/ 0811x/superhypoid.pdf , pp. 42-48.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

JOINTED CONTROL PLATFORM

CROSS-REFERENCE TO RELATED APPLICATIONS

This patent application is a continuation of U.S. application Ser. No. 16/269,159 (filed Feb. 6, 2019) (entitled "JOINTED CONTROL PLATFORM"), which claims priority to and the filing date benefit of U.S. Provisional Patent Application No. 62/628,133 (filed Feb. 8, 2018) (entitled "JOINTED CONTROL PLATFORM"), each of which is incorporated herein by reference in its entirety.

FIELD

Embodiments of the invention relate to the field of mechanical couplers; and more specifically, to a mechanical coupler for transferring motion from a teleoperated actuator to an attached surgical instrument.

BACKGROUND

Minimally invasive medical techniques have been used to reduce the amount of extraneous tissue which may be damaged during diagnostic or surgical procedures, thereby reducing patient recovery time, discomfort, and deleterious side effects. Traditional forms of minimally invasive surgery include endoscopy. One of the more common forms of endoscopy is laparoscopy, which is minimally invasive inspection or surgery within the abdominal cavity. In traditional laparoscopic surgery, a patient's abdominal cavity is insufflated with gas, and cannula sleeves are passed through small (approximately 12 mm) incisions in the musculature of the patient's abdomen to provide entry ports through which laparoscopic surgical instruments can be passed in a sealed fashion.

The laparoscopic surgical instruments generally include a laparoscope for viewing the surgical field and surgical instruments having end effectors. Typical surgical end effectors include clamps, graspers, scissors, staplers, and needle holders, for example. The surgical instruments are similar to those used in conventional (open) surgery, except that the working end or end effector of each surgical instrument is separated from its handle by an approximately 30 cm. long extension tube, for example, so as to permit the operator to introduce the end effector to the surgical site and to control movement of the end effector relative to the surgical site from outside a patient's body.

In order to provide improved control of the working tools, it may be desirable to control the surgical instrument with teleoperated actuators. The surgeon may operate controls on a console to indirectly manipulate the instrument that is connected to the teleoperated actuators. The surgical instrument is detachably coupled to the teleoperated actuators so that the surgical instrument can be separately sterilized and selected for use as needed instrument for the surgical procedure to be performed. The surgical instrument may be changed during the course of a surgery.

It will be appreciated that it is desirable to minimize the diameter of the extension tube, which couples the end effector to the teleoperated actuators, to minimize the size of the incision necessary to introduce the surgical instrument to the surgical site. Teleoperated surgical instruments may have cables or bands that transfer the motion of the teleoperated actuators from a proximal control mechanism at a proximal end of the extension tube to the end effector at a distal end of the tube. The cables or bands may form a loop with two proximal ends in the proximal control mechanism. One proximal end may be pulled to apply a force to the end effector while the other proximal end is payed out to maintain an appropriate tension in the loop.

Rotary actuators, such as electric motors, are an effective way to provide controlled actuation forces to a teleoperated surgical instrument. The proximal control mechanism translates the rotary input force into the push-pull motions of the two proximal ends needed to control the end effector. The proximal control mechanism may receive many such rotary inputs, perhaps four to eight, each of which can be translated into an appropriate motion for controlling some aspect of the end effector. It is desirable that the proximal control mechanism be compact to avoiding crowding in the surgical field.

In view of the above, it would be desirable to provide an improved apparatus and method for transmitting actuating forces to cables or bands intended for use in teleoperated minimally invasive surgeries.

SUMMARY

A force transmission mechanism includes a chassis having a pivotal support that defines a first axis of rotation. An axle is supported by the pivotal support and is free to rotate around the first axis of rotation. The axle defines a second axis of rotation perpendicular to the first axis of rotation. A first control arm is coupled to a first end of the axle and is free to rotate around the second axis of rotation. A second control arm is coupled to an opposite second end of the axle and is free to rotate around the second axis of rotation independently of the first control arm. An end effector is coupled to an elongate tube that is coupled to the chassis. Four drive elements coupled to the control arms control motions of the end effector.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

3

Figure 7:
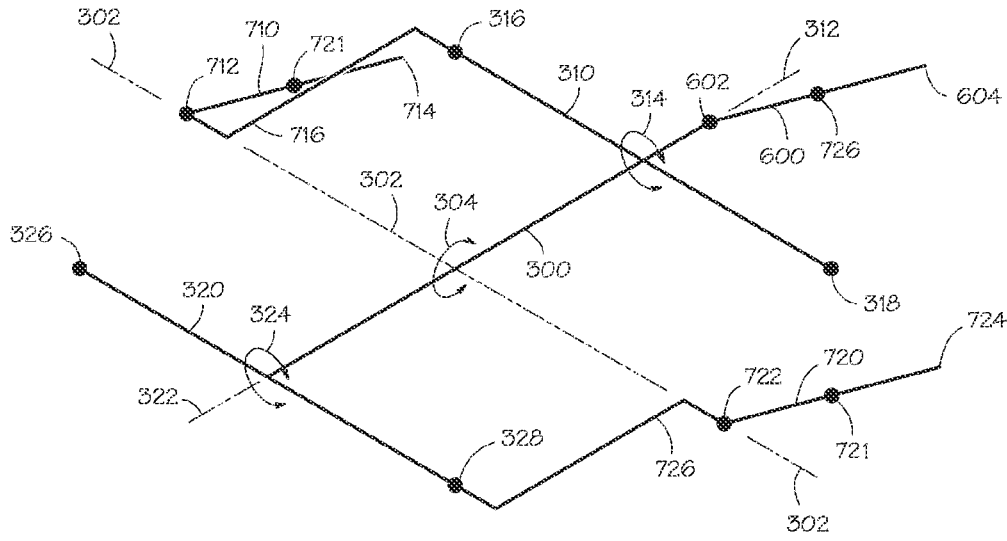
FIG. 7 is a schematic representation of another mechanism for moving the force transmission shown in FIGS. 3, 4, and 5.
Figures 10, 11:
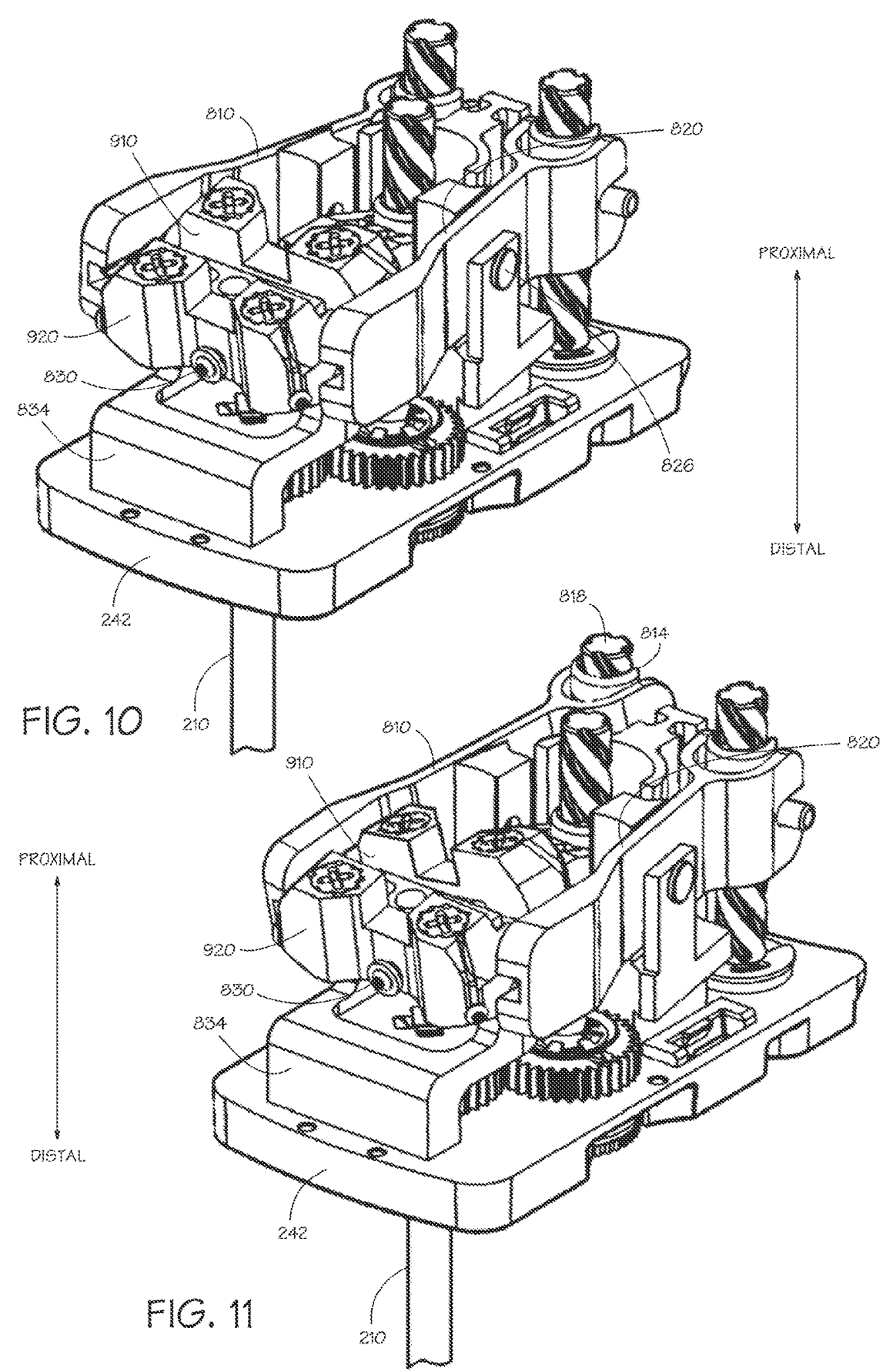

FIG. 10 is a pictorial view of the implementation of the force transmission shown schematically in FIG. 7.

FIG. 11 is a pictorial view of the implementation of the force transmission shown schematically in FIG. 7 in another operative position.

Figures 12, 13:
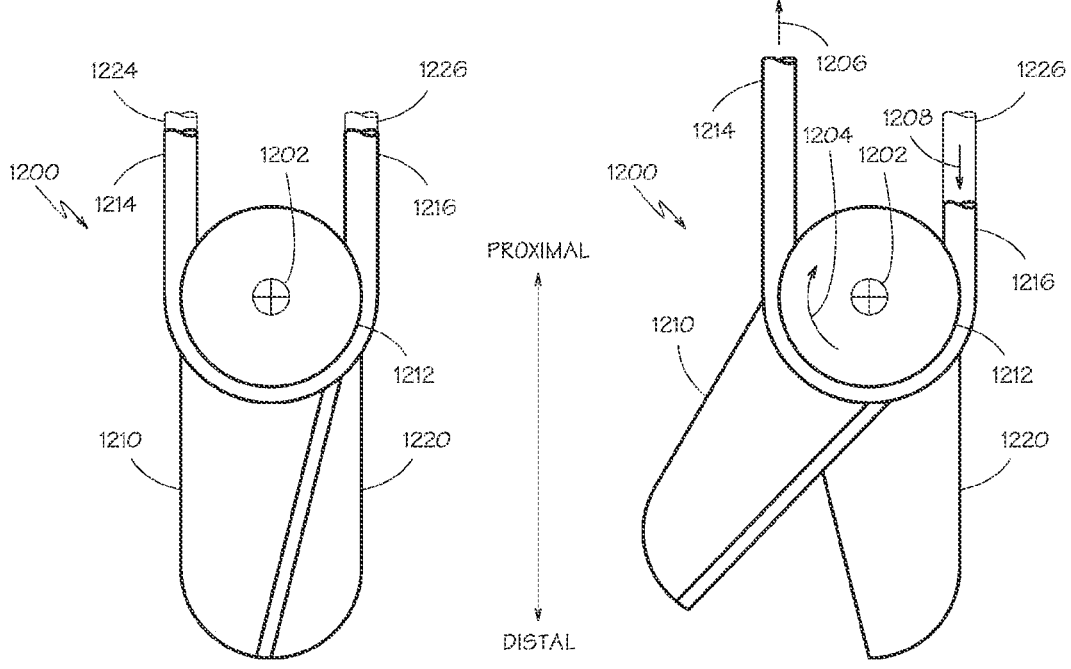

FIG. 12 is an illustration of an end effector demonstrating an application of the force transmission.

FIG. 13 is an illustration of the end effector of FIG. 12 in another operative position.

Figures 14, 15:
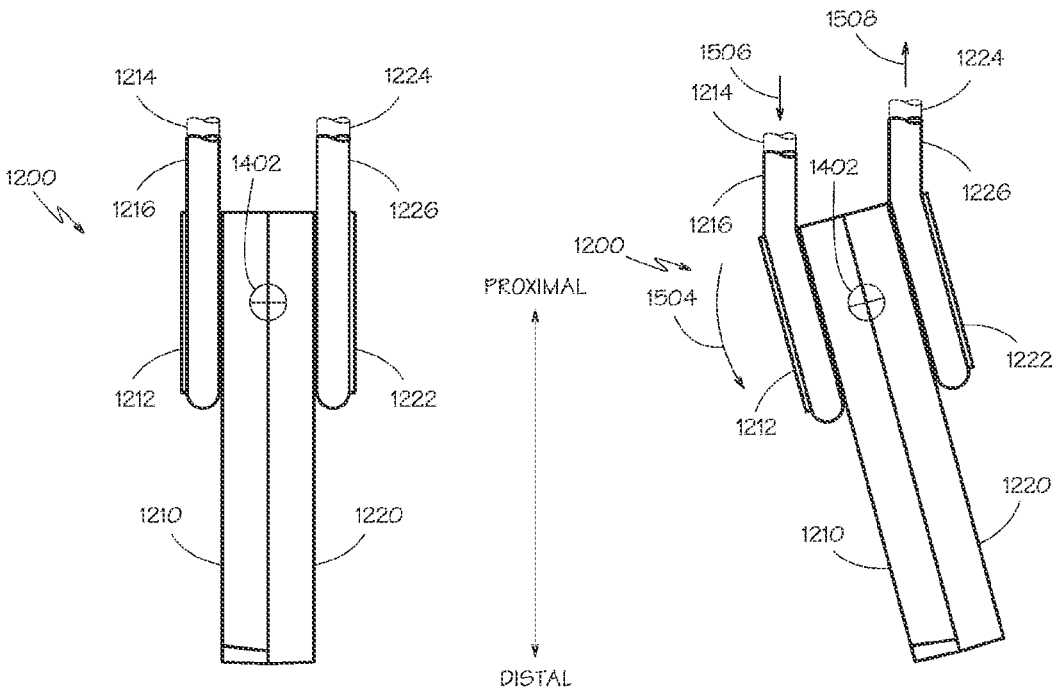

FIG. 14 is a side view of the end effector of FIG. 12.

FIG. 15 is a side view of the end effector of FIG. 12 in yet another operative position.

DESCRIPTION OF EMBODIMENTS

In the following description, numerous specific details are set forth. However, it is understood that embodiments of the invention may be practiced without these specific details. In other instances, well-known circuits, structures, and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a," "an," and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive, meaning any one item in a group or any combination of items in the group. Therefore, "A, B, or C" or "A, B, and/or C" mean "any of the following: A; B; C; A and B; A and C; B and C; A, B and C." An exception to this definition will occur only when a combination of elements, functions, steps or acts are in some way inherently mutually exclusive.

The term "object" generally refers to a component or group of components. For example, an object may refer to either a pocket or a boss of a disk within the specification or claims. Throughout the specification and claims, the terms "object," "component," "portion," "part," and "piece" are used interchangeably.

The terms "instrument" and "surgical instrument" are used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some instruments used with embodiments of the invention further provide an articulated support (sometimes referred to as a "wrist") for the surgical end effector so that the position and orientation of the surgical end effector can be manipulated with one or more mechanical degrees of freedom in relation to the instrument's shaft or chassis. Further, many surgical end effectors include one or more functional mechanical degrees of freedom, such as one or more jaws that open or close, or a knife that translates along a path.

Figures 1, 2:
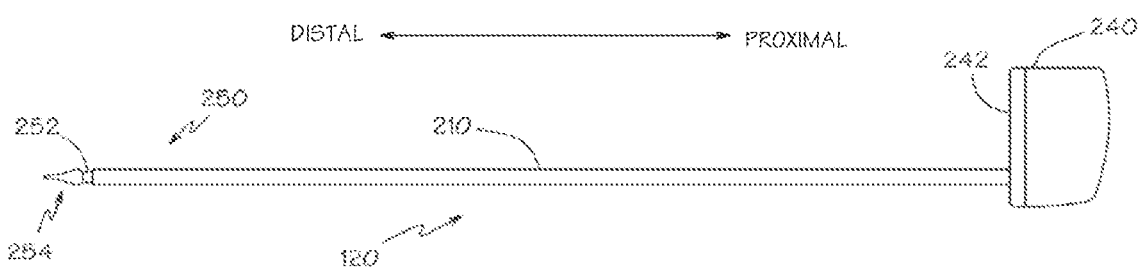
FIG. 1 is a view of an illustrative manipulating system of a teleoperated surgical system.
FIG. 2 is a side view of a surgical instrument for use with a teleoperated actuator.

FIG. 1 shows a pictorial view of a portion of a minimally invasive teleoperated surgical system. The portion shown is placed adjacent a surgical patient 122 to support the surgical instruments and provide teleoperated actuators that control the surgical instruments. This portion of the teleoperated surgical system may be termed a manipulating system 100. Typically, three or four surgical instruments 120, including a camera instrument that provides images of the surgical site and other instruments at the surgical site, are supported by the manipulating system 100. It will be appreciated that a minimally invasive teleoperated surgical system uses a substantial amount of equipment located in a small amount of space adjacent the surgical patient 122. While the manipulating system 100 is shown as providing four surgical instrument manipulators 130, other numbers of surgical instrument manipulators may be provided, such as one, two, three, or more than four. In some configurations, the teleoperated surgical system may include more than one manipulating system. Examples of manipulating systems are included in the da Vinci® Surgical System Models IS1200, IS2000, IS3000, and IS4000 commercialized by Intuitive Surgical, Inc., Sunnyvale, California. Manipulating systems include various ways in which they may be mechanically grounded, such as a cart that rolls on the floor, a ceiling mount, a patient operating table mount, and the like. An example of how a manipulating system may be combined with the operating table are the manipulators and manipulator positioning arms used for the Zeus® Surgical System commercialized by Computer Motion, Inc. and shown, for example, in U.S. Pat. No. 6,728,599 B2 (filed Sep. 7, 2001).

In practice, a manipulator 130 may move the surgical instrument 120 as a whole, and it may also transmit force to the instrument to move one or more instrument components, such as a wrist or jaw mentioned above. In the example shown, the teleoperated surgical instruments 120 are each coupled to a corresponding instrument carriage on a manipulator 130. The instrument carriage houses the teleoperated actuators that provide the mechanical power that is transmitted to the instrument. In some configurations, the teleoperated actuators are housed elsewhere in the manipulator or in a supporting arm. The teleoperated actuators allow a surgeon to manipulate the surgical instrument using a computer-operated user control station (not shown) that provides computer-assisted teleoperation. These manipulations may include functions such as changing the position and orientation of the surgical instrument's end effector and operating the end effector, such as closing jaws to effect grasping, cutting, etc. Such actuator control of surgical instruments may be referred to by various terms, such as teleoperated surgery. Each manipulator 130 may be supported on a separate structural arm 110 that, once positioned, can be fixed relative to the surgical patient 122. In various implementations the supporting arm 110 may be manually positioned, may be positioned via teleoperation by the surgeon, or may be automatically positioned by the system as the surgeon moves one or more of the surgical instruments 120.

A control system couples the computer-assisted user control station to the teleoperated actuators. Here "computer" broadly encompasses a data processing unit that incorporates a memory and an additive or logical function, such as an arithmetic logic unit, that is programmable to perform arithmetic or logical operations. The computer-assisted user control station includes one or more hand-operated control input devices that allow manipulation of the teleoperated slave surgical instruments 120 by transmitting signals, such as electrical or optical control signals, to the actuators that control the actions of the coupled teleoperated surgical instruments. In this way a master-slave relationship is established between the control input device of the user control station and the surgical instrument of the manipulating system.

The hand-operated control input devices, and the images of the surgical site and instruments at the surgical site provided by a camera instrument, may be arranged to provide an intuitive control of the surgical instruments 120, in which the instruments move in a manner similar to the operator's hand movements with the controllers. The movement of the surgical instruments 120 as displayed to the surgeon may appear at least substantially connected to the control input devices in the hands of the surgeon. Further levels of connection, such as force or other haptic feedback, may be provided to enhance the surgeon's dexterity and ease of use of the surgical instruments 120. One, two, three, or more actuators may be provided to move the end effector of the associated surgical instrument 120 with one or more mechanical degrees of freedom (e.g., all six Cartesian degrees of freedom, five or fewer Cartesian degrees of freedom, jaw grip, etc.).

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of surgical end effectors 254, such as the forceps shown, a needle driver, a cautery device, a surgical stapler, a cutting tool, an imaging device (e.g., an endoscope or ultrasound probe), or a combined device that includes a combination of two or more various tools and imaging devices. In the embodiment shown, the surgical end effector 254 is coupled to the elongate tube 210 by a wrist 252 that allows the orientation of the surgical end effector to be manipulated with reference to the elongate tube 210. In addition, the tube 210 may rotate around its long axis so that the end effector 254 correspondingly rolls around its long axis. The end effectors and the wrist illustrate various movable distal components of the surgical instrument.

Surgical instruments that are used with the surgical invention may control their end effectors, wrists, or any intervening jointed or flexible section with a plurality of any combination of drive elements, such as tension (pull) elements, compression (push) elements, or combined tension/compression elements. Examples of these drive elements include flexible cables and/or bands, push and/or pull rods, cable/hypotube combinations, Bowden cables, and the like, and they may be made of materials such as steel, tungsten, or polymer (e.g., Dyneema® polyethylene). It will be appreciated that the drive elements should be inelastic and also as flexible as necessary so that pulling and/or pulling forces can be transmitted by the drive elements as they bend around pulleys and guides.

A typical elongate tube 210 for a surgical instrument 120 is small, often in a range of five to eight millimeters in diameter, although they may be larger (e.g., 14 mm) or smaller (e.g., 3 mm). The diminutive scale of the mechanisms in the surgical instrument 120 creates unique mechanical conditions and issues with the construction of these mechanisms that are unlike those found in similar mechanisms constructed at a larger scale, because forces and strengths of materials do not scale at the same rate as the size of the mechanisms. The drive elements must fit within the elongate tube 210 and be able to bend as they pass through the wrist joint 252.

In a teleoperated surgical instrument, mechanical force originating outside the instrument (e.g., at a teleoperated actuator) must be received into the instrument and then directed to the instrument component to be moved (e.g., the instrument shaft, a wrist, an end effector). Various mechanisms have been designed to carry this out. For example, force (the term "force" as used herein includes torque) may be received into the instrument via a rotating actuator output disk mated with an instrument input disk, or via a moving actuator output lever or gimbal mated with an instrument input lever or gimbal, or via a translating linear actuator drive mated with an instrument linear input. Once the drive force is received at the instrument, it is then directed to one or more drive elements by way of mechanisms inside the instrument, such as capstans and cables, levers, gimbals, gears, pulleys, and the like.

Figure 3:
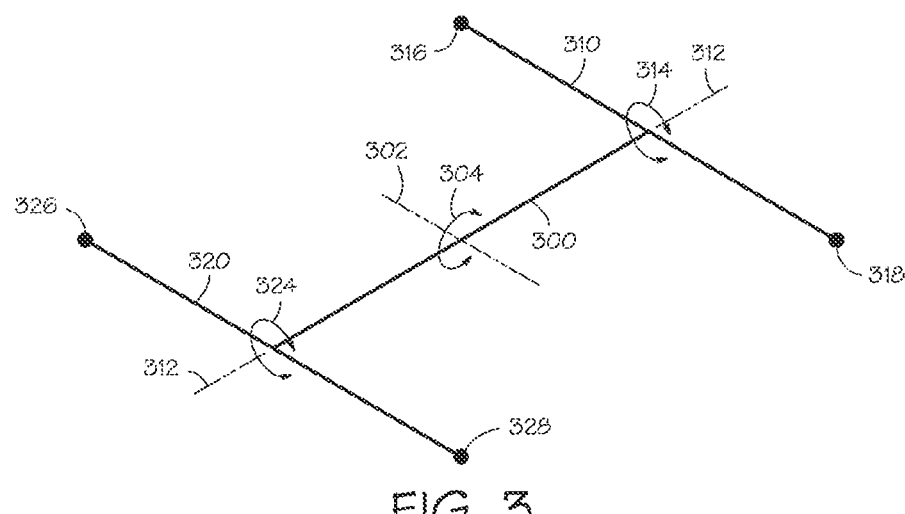
FIG. 3 is a schematic representation of an embodiment of a force transmission that can be used to control an end effector of a surgical instrument.

FIG. 3 is a schematic representation of an embodiment of a jointed control platform mechanism in a force transmission pathway inside an instrument between proximal multiple force inputs and multiple drive elements in the instrument. As discussed above, these drive elements are used to control one or more distal components of the instrument, such as an end effector or wrist. Two control arms 310, 320 are shown. Each control arm 310, 320 has two control points, one control point at the opposite end of each arm. As shown, control point 316 is at one end of arm 310, and control point 318 is at the opposite end of arm 310. Similarly, control point 326 is at one end of arm 320, and control point 328 is at the opposite end of arm 320. As described in more detail below, a unique drive element is attached to a corresponding unique control point, so that each drive element is moved as the corresponding arm moves. Since there are four control points, four drive elements are coupled to the combination of the two control arms. The drive elements are then routed to the distal end of the instrument.

The two control arms 310, 320 are coupled together by an axle 300. Arm 310 is coupled to one end of axle 300 between control points 316 and 318, and arm 320 is coupled to the opposite end of axle 300 between control points 326 and 328. Arms 310 and 320 are each pivotally mounted to the axle 300 so that they independently rotate at the ends of axle 300. Optionally arms 310 and 320 are mounted to opposite ends of axle 300, and an axial roll joint (not shown) allows the opposite ends of axle to roll with respect to one another, thus allowing the arms to rotate with respect to one another. The long axis 312 of axle 300 defines a common axis of rotation for both arm 310 and 320, so that each arm rotates about the common axis 312. Each control arm has one rotational degree of freedom with respect to the axle.

The axle 300 is pivotally supported to permit axle 300 to rotate about an axis 302 that is orthogonal to axis 312 and that extends in the same general directions as arms 310 and 320. As shown, axis 312 is midway between the ends of axle 300 at which arms 310, 320 are coupled. Axle 300 has one rotational degree of freedom with respect to a ground plane that supports the axis of rotation 302 for the axle. It can be seen that as axle 300 rotates 304 around axis 302, arm 310 moves closer to the ground plane as arm 320 moves away from the ground plane, and vice versa. It can further be seen that each one of the control points 316, 318, 326, 328 can be moved closer to or farther from the ground plane in one of two ways—by rotating 314, 324 an individual arm 310, 320 with reference to axis 312 of axle 300, or by rotating 304 axle 300 with reference to axis 302.

In the schematic of FIG. 3, the four control points 316, 318, 326, 328 are equally and symmetrically spaced such that the four control points are located at the vertices of a square when the four control points are coplanar. Thus curvilinear translation in space (approximately perpendicular to the plane defined by axes 302 and 312) of one control point on an arm will result in an equal curvilinear translation in space of its corresponding opposite control point on the arm as the arm rotates about axis 312. Similarly, curvilinear translation in space (again, approximately perpendicular to the plane defined by axes 302 and 312) of one control point on one control arm will result in an equal curvilinear translation in space of its corresponding mirrored control point, or its corresponding opposite control point, on the other arm as axis 300 rotates about axis 302. Therefore, various combinations of rotations around both axes 302 and 312 will result in translations of the four control points that in turn will result in various equal translations of drive elements attached at each control point. Equal translation of associated drive elements is required if a distal component of the surgical instrument requires equal translation to operate properly (e.g., equal and opposite cable pay-in and pay-out over a pulley, push rod translations to move a class 1 lever, and the like).

It can also be seen that the control points need not be at the physical ends of the levers, but may be at any location along the levers equidistant from axle 300 (axis 312) that provides the necessary geometric relation between the four control points. And, the length of axle 300 between arms 310, 320 can likewise be varied to provide the necessary geometric relation between the four control points. Thus when the control points are coplanar they can be at any positions along the arms 310, 320 and spaced apart by axle 300 to define any four-sided polygon necessary to provide the required displacement of the associated drive elements as the arms 310, 320 rotate around axis 312 and the axle rotates around axis 302. It can further be seen that if the control points are kept coplanar, then the mechanism functions as a two degree of freedom gimbal, but when the control points are allowed to move off coplanar alignment, many additional control point positions are possible when compared to a normal gimbal. These observations also apply to the following embodiments.

Figure 4:
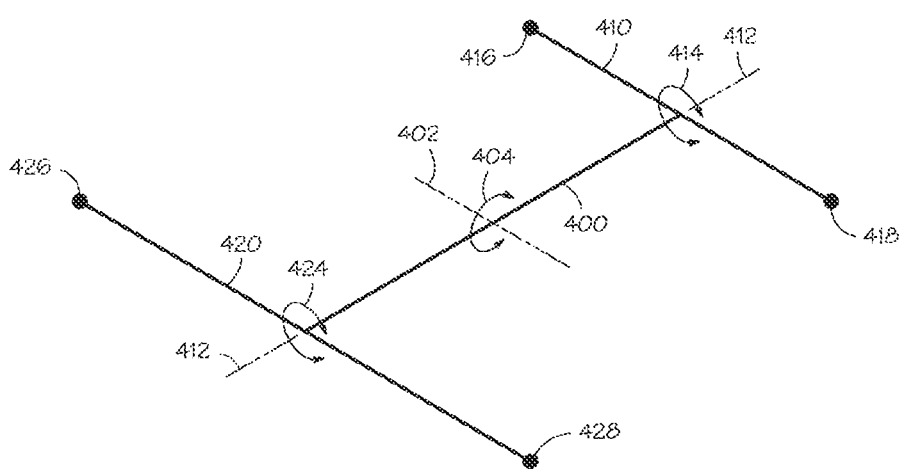
FIG. 4 is a schematic representation of another embodiment of a force transmission.

FIG. 4 is a schematic representation of another jointed control platform mechanism in a force transmission pathway inside an instrument between multiple force inputs and multiple drive elements in the instrument. The mechanism illustrated by FIG. 4 is similar to the mechanism in FIG. 3, but one control arm 420 is longer than the other control arm 410. Each control arm 410, 420 is pivotally mounted to an axle 400 midway between the control points 416, 418, 426, 428 on the control arm. When the four control points are coplanar, the four control points are located at the vertices of an isosceles trapezoid, in which the axle 400 forms a line of symmetry for the trapezoid. It can be seen that although curvilinear translations of the control points on each individual arm will be equal as the arm rotates 414, 424 around axis 412, curvilinear translations of the control points on the opposite arms will not be equal if the arms rotate through an equal angle around axis 412. In some instances, however, the individual arms may be rotated by different angles around axis 412 so that equal curvilinear translation of one set of opposite control points (416, 428 or 418, 426) occurs. If the arms 410, 420 are equidistant from axis 402 on axle 400, then as axle 400 rotates 404 around axis 402 the curvilinear translations of the control points on one arm will be equal to the curvilinear translations of the control points the other arm. If the arms 410, 420 are not equidistant from axis 402 on axle 402, then as illustrated below curvilinear translations of control points of the two arms may or may not be equal, depending on the positions along which each arm 410, 420 joins axle 400.

Figure 5:
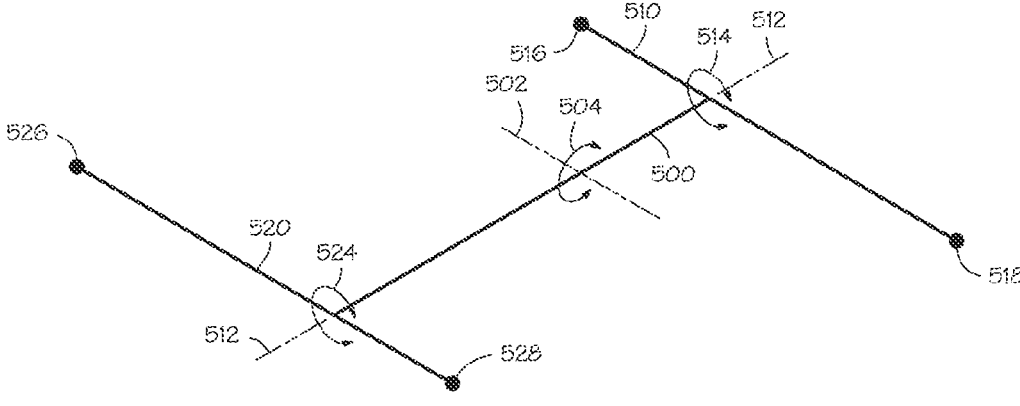
FIG. 5 is a schematic representation of yet another embodiment of a force transmission.

FIG. 5 is a schematic representation of another jointed control platform mechanism in a force transmission pathway inside an instrument between multiple force inputs and multiple drive elements in the instrument. The mechanism illustrated by FIG. 5 is similar to the mechanism in FIG. 3, but each control arm 510, 520 is pivotally mounted to an axle 500 so that the distances between the control points on the arm and the axle 500 are not equal. Therefore, as an arm rotates 514, 524 around the axis of rotation 512 defined by axle 500, the curvilinear translation of the opposite control points on the arm is not equal. Optionally, or in addition, the distances between the ends of the axle 500 and its axis of rotation 502 are not equal. Therefore, as axle 500 rotates 504 around axis 502, the curvilinear translations on the control arms will be unequal. It can be seen, however, that various combinations of rotations of arms 510, 520 around axis 512 can result in equal curvilinear translations of either mirrored or opposite pairs of control points on the two arms. Likewise, various combinations of rotations or arms 510, 520 around axis 512 and rotation of axle 500 around axis 502 can result in equal curvilinear translations of two control points.

FIGS. 3 through 5 are intended to show some of the possible embodiments of a mechanism that can be used to control a distal end component of a surgical instrument. Further variations are possible including, but not limited to, mounting only one of the control arms so that the distances between the control points and the axle are not equal or mounting one or more control arms of differing lengths so that the distances between the control points and the axle are not equal. Such variations may be made to meet the requirements for controlling a particular distal end component of a surgical instrument with various translations of the associated drive elements.

Figure 6:
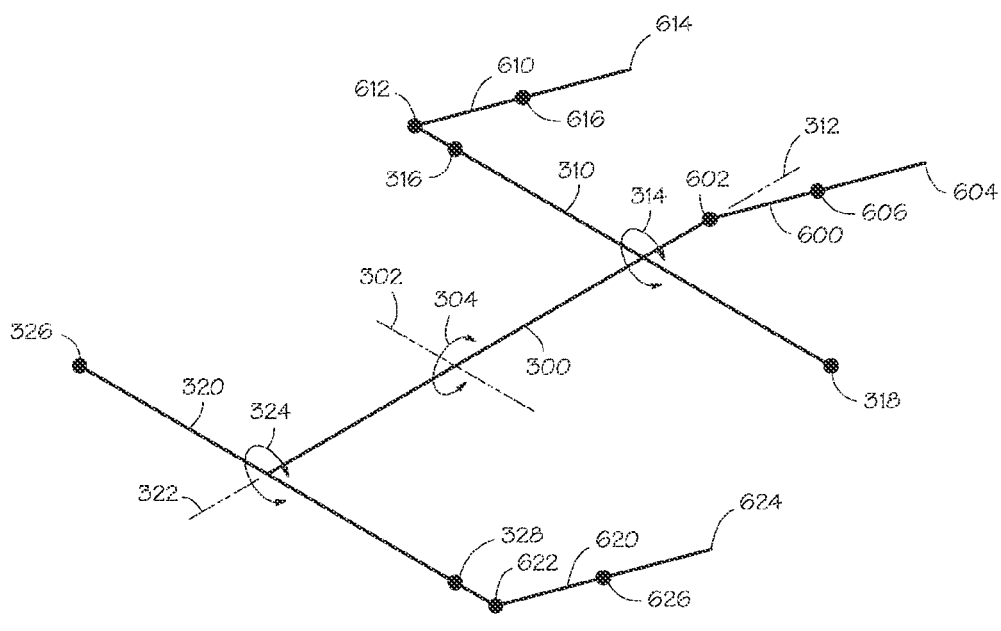
FIG. 6 is a schematic representation of a mechanism for moving the force transmission shown in FIGS. 3, 4, and 5.

FIGS. 6 and 7 are schematic representations of mechanisms in a force transmission pathway inside an instrument between multiple force inputs and multiple drive elements in the instrument. As described below, it is possible to use three force inputs to control the four drive elements and so not only reduce the overall complexity and cost of an instrument, but reduce the complexity and cost of the manipulator required to operate the instrument with four independently controlled drive elements.

FIGS. 6 and 7 illustrate embodiments of force inputs to the mechanisms shown in FIGS. 3-5. In general, various force input components may be coupled to the mechanisms illustrated in FIGS. 3-5 in order to either move the control arms individually or together as a unit. The force inputs shown in FIGS. 6 and 7 are described with the use of levers, but other inputs such as cables, lead screw and nut combinations, cams, and the like may be used. Levers provide a compact and robust way of controlling axle 300 and arms 310, 320, as illustrated below. And, although class 1 levers are shown, class 2 and class 3 levers are optionally used.

As shown in FIG. 6, a class 1 lever 600 is coupled to the axle 300 to rotate the axle around the axis 302 of its pivotal support as illustrated by the arrows 304 (see also FIG. 3). The lever 600 is illustrated as a class 1 lever with a fulcrum 606 between the force input coupling (resistance) point 602 at the axle and the force input (effort) point 604 for force applied to the lever from the instrument manipulator. The coupling between the lever 600 and the axle 300 accommodates the changing distance between the coupling point 602, the fulcrum 606, and the axis 302 of the pivotal support of the axle, such as a pin and slot combination or the like. Coupling point 602 is shown outboard of arm 310, but optionally coupling point 602 is at any position between arm 320 and arm 310 sufficient to cause the required force on the drive elements coupled to the control points as axle 300 rotates around axis 302.

A second lever 610 is coupled to one of the control arms 310 to rotate control arm around axis 312 at its pivotal coupling to the axle 300, as illustrated by the arrows 314. The coupling between the second lever 610 and the control arm 310 accommodates the changing distance between the input coupling (resistance) point 612, the fulcrum 616, and the axis 312 of the pivotal support of the control arm, such as with a ball and slot combination. Force input is applied at force input (effort) point 614. Input coupling point 612 is shown outboard of control point 316, but optionally coupling point 612 is at any position between control point 316 and control point 318 sufficient to cause the required force on the drive elements coupled to the control points as arm 310 rotates around axis 312.

A third lever 620 is similarly coupled to the other of the control arms 320. As shown in FIG. 6, third lever 620 is coupled to control arm 320 in a similar manner to the way second lever 610 is coupled to control arm 310. Lever 620 is coupled to arm 320 at input coupling (resistance) point 622, with fulcrum 626 and force input (effort) point 624 being similar to fulcrum 616 and force input point 614 of second lever 610. As shown, input coupling point 622 is on an opposite side of axis 312 from input coupling point 612, but optionally it may be at any position on arm 320 as described above for coupling point 612 on arm 310.

It can be seen that on the condition that second lever 610 and third lever 620 do not move, then rotating axle 300 around axis 302 with the first lever 600 will also cause the control arms 310, 320 to rotate around axis 312. And, the necessary dimensions being equal, the rotations will be of equal magnitude. On the condition that lever 600 does not move, then lever 610 controls rotation of arm 310 around axis 312, and lever 620 controls rotation of arm 320 around axis 312, these two rotations being independent. On the condition that lever 600 rotates axle 300 around axis 302, lever 610, lever 620, or both, may be moved to keep one or more control points 316, 318, 326, and 328 at a desired location in space, or to create various combinations of locations in space for these control points that are used to control position or orientation of a distal end component of the instrument. Thus with various combinations of inputs (efforts) on the three levers, various combinations of curvilinear translations of the four control points and associated drive elements may be obtained.

As shown in FIG. 7, the second and third levers 710, 720 are coupled to the control arms 310, 320 by extension arms 716, 726 so that the coupling points 712, 722 lie on the axis of rotation 302 for the axle 300 when the four control points 316, 318, 326, 328 are coplanar. In this position, rotating the axle 300 around axis 302 with the first lever 700 causes both control points 316, 318 on control arm 310 to move with respect to the two control points 326, 328 on control arm 320 without rotating the control arms 310, 320 and moving the two control points on each control arm with respect to one another. Thus, with coupling points 712 and 722 positioned on axis 302, motion of lever 600 moves the mechanism only around axis 302, and no rotations around axis 312 occurs. Rotations of arms 310, 320 around axis 312 is carried out by rotating levers 710, 720 around their fulcrums 711, 721.

While FIGS. 6 and 7 show the use of levers coupled to the mechanism shown in FIG. 3, it will be appreciated that levers can be similarly coupled to the mechanisms shown in FIGS. 4 and 5.

Figures 8, 9:
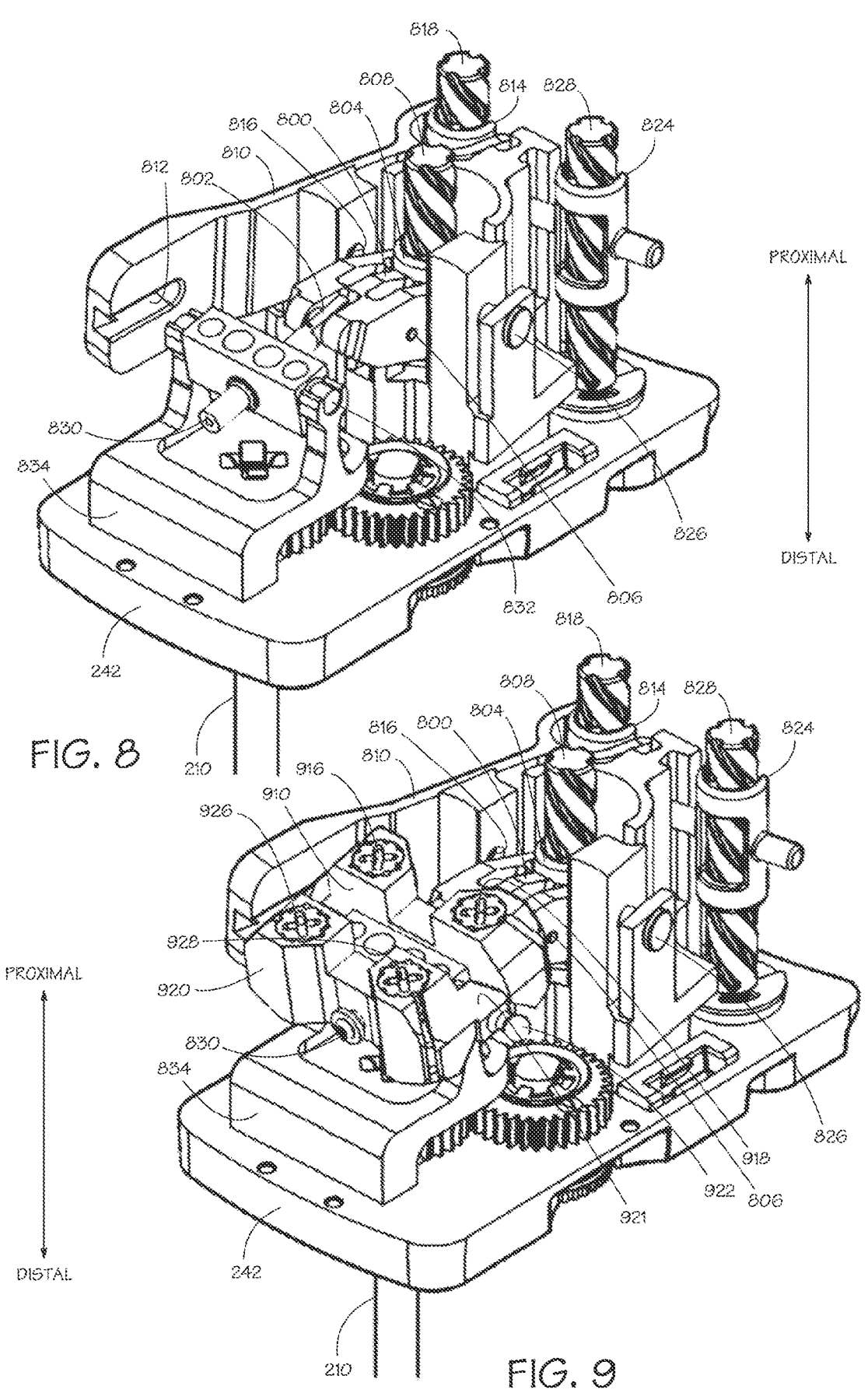
FIG. 8 is a pictorial view of a partial assembly of an implementation of the force transmission shown schematically in FIG. 7.
FIG. 9 is a pictorial view of another partial assembly of the implementation of the force transmission shown schematically in FIG. 7.

FIGS. 8 through 11 illustrate an implementation of the force transmission shown schematically in FIG. 7 that could be applied to the proximal control mechanism 240 of the surgical instrument 120 shown in FIG. 2. FIGS. 8 and 9 show the mechanism with some parts removed to allow the remaining parts to be seen more clearly.

FIG. 8 is a pictorial view of a partial assembly of the implementation of the force transmission shown schematically in FIG. 7. The proximal end of the elongate tube 210 is coupled to a base chassis 242 that provides the ground plane for the force transmission used to control the end effector 254 of the surgical instrument 120.

An axle 830 is supported by a pivotal support 832 having an axis of rotation perpendicular to the midpoint of the longitudinal axis of the axle. The pivotal support 832 is supported by a bracket 834 coupled to the base chassis 242. The axle 830 thus has one degree of rotational freedom with respect to the ground of the base chassis 242.

A first lever 800 is coupled at a coupling point 802 to the axle 830 to rotate the axle around the axis of rotation defined by pivotal support 832. The first lever 800 is supported by a fulcrum 806 that is supported by the base chassis 242, which provides a ground structure for the proximal control mechanism. The coupling between the lever 800 and the axle 830 accommodates the changing distance between the coupling point 802, the fulcrum 806, and the pivotal support 832 of the axle. As shown, this coupling 802 is a slot and pin. Effort is applied to the lever by a high pitch screw 808 and thread follower 804 with a tight tolerance between the screw and follower to minimize backlash for effective control.

FIG. 9 is a pictorial view of a partial assembly of the implementation of the force transmission shown schematically in FIG. 7 in which the two control arms 910, 920 are shown. Control points 916 and 918 are on opposite ends of arm 910, and control points 926, 928 are on opposite ends of arm 920. Each control arm 910, 920 is pivotally mounted on the axle 830 to permit rotation about a common axis defined by the longitudinal axis of axle 830, such that each control arm has one degree of rotational freedom and is otherwise constrained with respect to the axle. Four drive elements (bands or cables; hidden from view underneath arms 910 and 920) are coupled to corresponding individual control points 916, 918, 926, 928 and extend through bracket 834 and into tube 210.

As described above, second lever 810 is supported by a fulcrum 816 that is supported by the base chassis 242. Each control arm 910, 920 includes an extension arm 921 (analogous to arms 716 and 726 in FIG. 7) so that the coupling point 922 between the control arm and the coupled lever lies on the axis of rotation for the pivotal support 832 of the axle 800 when the four control points 916, 918, 926, 928 are coplanar. A ball and slot coupling is provided between the control arm and the coupled lever to provide a motion-accommodating coupling. A ball is shown on the coupling point 922 of control arm 920. A slot 812 is shown in FIG. 8 on the second lever 810 that will be coupled to a ball on control arm 910 similar to the ball at coupling point 922 of control arm 920.

FIG. 10 is a pictorial view of the implementation of the force transmission shown schematically in FIG. 7 in which all components implementing the schematic representation are shown. A third lever 820 is supported by a fulcrum 826 that is supported by the base chassis 242. The third lever 820 is coupled to the coupling point 922 of control arm 920 with a motion-accommodating coupling as described above. The third lever 820 couples a third lead screw 828 and thread follower 824 to the control arms 920.

FIG. 11 is a pictorial view of the implementation of the force transmission shown schematically in FIG. 7 in which control arm 910 has been rotated around axle 830 with respect to control arm 920. One of the lead screws 818 has been rotated to raise the thread follower 814 at the effort end of the second lever 810. The second lever 810 is a class 1 lever, and the resistance end, which is coupled to the control arm 910, causes the control arm to rotate about the supporting axle 830.

Thus as illustrated, three rotational inputs to the surgical instrument are transformed to four individually-controllable drive elements in a compact, robust, and economical mechanism.

Other mechanisms may be used to move the axle and control arms of the mechanisms shown schematically in FIGS. 3 through 5 in place of the levers shown in FIGS. 6 through 11. For example, a lead screw and thread follower may optionally be connected directly to the axle and/or control arms of the force transmission or connected via other coupling mechanisms such as push rods. The axle and control arms may optionally all be moved by the same type of mechanism or optionally a combination of different types of mechanisms may be used. Rotational or linear actuators may be directly or indirectly coupled to the axle and control arms.

FIGS. 12 through 15 illustrate an end effector 1200—a surgical shear is illustrated—to demonstrate how the mechanism may be used to control an end effector of a surgical instrument. The mechanism is not limited to controlling this type of end effector, or controlling the end effector in the manner shown, or controlling an end effector. These figures are merely to show an exemplary use of the force transmission as an aid to further understanding the mechanism's characteristics.

FIG. 12 shows the end effector 1200, which includes two jaws 1210, 1220 coupled by a pivot 1202 such that each jaw can rotate independently about the pivot. Each jaw is coupled to an associated pulley 1212, 1222. A corresponding drive element control loop, which may be formed from one or more flexible cables and/or bands, passes over a pulley to rotate the pulley and the coupled jaw. The control loop may include non-flexible drive element sections that couple flexible sections.

Two control loops may be used to control motions of the end effector. Each loop may independently control a motion of the end effector. For example, each loop may control the angular position (arbitrarily termed "yaw") of one of two blades of a pair of shears. By coordinating the motions of the two loops, the blades of the shears can be opened and closed with respect to one another. Both blades can also be moved in the same direction (arbitrarily termed "pitch") to position the shears at an angle that is offset from the longitudinal axis of the elongate tube.

Each control loop is moved by moving the two proximal ends 1214, 1216, 1224, 1226 of the drive element loop. It will be appreciated that the pulley mechanism is a "length conserving" control mechanism in which the movement of one proximal end 1214, 1224 of the control loop is matched by an equally sized movement of the other proximal end 1216, 1226 in the opposite direction. Coupling the two proximal ends of a control loop to the two control points on a control arm that is pivotally coupled to an axle at the midpoint between the two control points ensures that the "length conserving" requirement for movement of the control loop is met. That is, the loop does not go slack as the pulley rotates, and a force can be maintained in both parts of the loop between the pulley and the control points in addition to the force on one side that is used to rotate the pulley.

FIG. 13 shows the end effector 1200 of FIG. 12 after one end 1214 of the control loop has been moved toward the proximal end of the surgical instrument by rotating the control arm and the other end 1216 of the control loop has moved toward the distal end. This is a "length conserving" movement of the control loop created by rotation of a symmetrically pivoted control arm, as suggested by the arrows 1206, 1208 on the control loop. The movement of the control loop causes the jaw 1210 coupled to the pulley 1212 over which the control loop passes to rotate, as suggested by the curved arrow 1204. The end effector may be used by rotating a single jaw as shown, by rotating both jaws in opposite directions, and by rotating both jaws in the same direction. The independent rotation of the two control arms of the force transmission provides the necessary movements of the ends of the control loops for all these jaw rotations.

FIG. 14 shows a side view of the end effector 1200 of FIG. 12. The end effector 1200 is pivotally supported on a wrist pivot 1402 having an axis that is perpendicular to an axis of the coupling pivot 1202 that couples the two jaws 1210, 1220. The axis of the wrist pivot 1402 is shown as intersecting the axis of the coupling pivot 1202 for simplicity. However, the axis of the wrist pivot 1402 may be displaced from the axis of the coupling pivot 1202.

FIG. 15 shows the end effector 1200 after being rotated about the axis of the wrist pivot 1402 as suggested by the curved arrow 1504. The rotation about the axis of the wrist pivot 1402 shown is controlled by moving both ends 1214, 1216 of the first loop in a distal direction, as suggested by the distally pointing arrow 1506, and moving both ends 1224, 1226 of the second loop in a proximal direction, as suggested by the proximally pointing arrow 1508. This needs to be a length conserving movement, which can be provided by control arms that are coupled to an axle that is pivotally supported at the midpoint between the two control arms.

When the coupling points between the control arms and the coupled levers lie on the axis of rotation for the pivotal support of the axle, the end effector 1200 can be rotated about the axis of the wrist pivot 1402 without rotating the jaws about the coupling pivot 1202. But if the coupling points do not lie on the axis of rotation for the pivotal support of the axle, it may be necessary to control the motion of the control arms to avoid rotation of the control arms on the axle and the resulting rotation of the jaws.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting. For example, aspects of the mechanism shown and described may optionally be adapted for use in a teleoperated surgical instrument or in any other medical device machine in which independent control of four separate drive elements is required, such as in a teleoperated manipulator that is providing output forces to an attached surgical instrument or in a hand-held device. Further, aspects of the mechanism may optionally have applications outside of the medical device industry, such as in various robotic, teleoperated, and other technologies.

What is claimed is:

1. A medical device including a proximal control mechanism for transferring motion from an actuator to a medical tool, comprising:

the proximal control mechanism, an elongate tube, a distal component, a first drive element, and a second drive element;

the distal component comprising the medical tool;

the elongate tube having a first end coupled to the proximal control mechanism and a second end opposite the first end, the second end coupled to the distal component;

the proximal control mechanism comprising a chassis supporting a pivotal support, an axle, and a control arm, the control arm being positioned entirely within a perimeter boundary of the chassis;

the pivotal support defining a first axis of rotation;

the axle comprising a first end and a second end opposite the first end, a second axis of rotation being defined through the first end of the axle and the second end of the axle, the axle being supported by the pivotal support so that the axle is free to rotate in the pivotal support around the first axis of rotation, and the second axis of rotation is perpendicular to the first axis of rotation;

a first control point being defined on the control arm, and a second control point being defined on the control arm spaced apart from the first control point;

the first end of the axle being coupled to the control arm between the first control point and the second control point, the control arm rotatable around the second axis of rotation;

the first drive element being coupled between the first control point and the distal component; and the second drive element being coupled between the second control point and the distal component.

2. The medical device of claim 1, further comprising:

a first drive input coupled to the axle at a first drive input coupling; and a second drive input coupled to the control arm at a second drive input coupling, wherein the control arm and the second drive input rotate relative to one another around the first axis of rotation at the second drive input coupling.

3. The medical device of claim 2, wherein:

the first drive input comprises a first lever, and the first drive input coupling comprises a first sliding coupling; and the second drive input comprises a second lever, and the second drive input coupling comprises a second sliding coupling.

4. The medical device of claim 1, wherein:

the first drive element and the second drive element form a first loop with reference to a first moving part of the distal component.

5. The medical device of claim 1, wherein:

the axle further comprises a first pin and a second pin opposite the first pin; and the axle is supported by the pivotal support at the first pin and the second pin.

6. The medical device of claim 1, wherein the control arm is a first control arm, the medical device further comprising:

a second control arm coupled to a second end of the axle, the first axis of rotation being equidistant from the first control arm and the second control arm.

7. The medical device of claim 6, wherein the first control arm and the second control arm are the same length.

8. The medical device of claim 6, further comprising:

a third control point and a fourth control point on the second control arm, the axle being between and spaced apart from the first, second, third, and fourth control points.

9. The medical device of claim 8, wherein the axle is equidistant from the first, second, third, and fourth control points.

10. The medical device of claim 1, further comprising:

a first lever coupled to the axle such that an effort applied to the first lever causes the axle to rotate about the first axis of rotation.

11. The medical device of claim 6, further comprising:

a first lever and a second lever, the first lever coupled to one of the first control arm and the second control arm, and the second lever coupled to the other one of the first control arm and the second control arm such that an effort applied to one of the first lever and the second lever causes the one of the first control arm and the second control arm to rotate about the second axis of rotation.

12. A medical device including a proximal control mechanism for transferring motion from an actuator to a medical tool, comprising:

means for pivotally supporting an axle that defines a first axis of rotation within the proximal control mechanism;

means for rotating the axle around the first axis of rotation, the axle having a first end, a second end opposite the first end, and a second axis of rotation defined between the first and second ends of the axle, the second axis of rotation being perpendicular to the first axis of rotation;

a first control arm coupled to the first end of the axle;

a second control arm coupled to the second end of the axle;

means for rotating the first control arm around the second axis of rotation; and means for rotating the second control arm around the second axis of rotation independently of rotation of the first control arm.

13. The medical device of claim 12, further comprising means for transferring motion of the first control arm and the second control arm to an end effector.

14. The medical device of claim 12, wherein the means for pivotally supporting the axle includes a chassis, the medical device further comprising:

an elongate tube having a proximal end portion coupled to the chassis; and

a medical tool coupled to a distal end portion of the elongate tube.

15. The medical device of claim 14, further comprising:

a first drive element coupled to the first control arm, extending through the elongate tube, and coupled to the medical tool;

a second drive element coupled to the second control arm, extending through the elongate tube, and coupled to the medical tool; and the rotation of the first control arm and the second control arm causing motion of the medical tool via the first drive element and the second drive element.

16. A medical device including a proximal control mechanism for transferring motion from an actuator to a medical tool, comprising:

a chassis pivotally supporting an axle, the chassis being within the proximal control mechanism and defining a first axis of rotation;

an elongate tube having a proximal end portion coupled to the chassis;

the medical tool coupled to a distal end portion of the elongate tube;

a control arm coupled to the axle and configured to rotate around the first axis of rotation, a lever coupled to the axle, the axle having a first end, a second end opposite the first end, and a second axis of rotation defined between the first end of the axle and the second end of the axle, the second axis of rotation being perpendicular to the first axis of rotation; and a lead screw coupled to the chassis and coupled to the lever, the lead screw configured to rotate the lever, which causes the control arm to rotate around the second axis of rotation.

17. The medical device of claim 16, further comprising:

a first control point defined on the control arm, and a second control point defined on the control arm spaced apart from the first control point,

the first end of the axle being coupled to the control arm between the first control point and the second control point.

18. The medical device of claim 16, wherein the control arm is a first control arm, the medical device further comprising:

a second control arm coupled to the axle and configured to rotate around the second axis of rotation, the lead screw configured to rotate the lever around the first axis of rotation, which causes the second control arm to rotate around the second axis of rotation independently of rotation of the first control arm.

19. The medical device of claim 18, further comprising:

a first control point defined on the first control arm, and a second control point defined on the first control arm spaced apart from the first control point;

a third control point defined on the second control arm, and a fourth control point defined on the second control arm spaced apart from the third control point; and the first end of the axle being coupled to the first control arm between the first control point and the second control point, and the second end of the axle being coupled to the second control arm between the third control point and the fourth control point.

20. The medical device of claim 16, further comprising:

a drive element coupled to the control arm, extending through the elongate tube, and coupled to the medical tool, and rotation of the control arm causes motion of the medical tool via the drive element.

21. The medical device of claim 1, wherein:

as the control arm rotates about the second axis of rotation, one of the first control point and the second control point moves from a first position to a second position closer to the chassis than the first position, and the other of the first control point and the second control point moves from a third position to a fourth position further from the chassis than the third position.

* * * * *